United States Patent
Vitello et al.

(10) Patent No.: US 10,315,024 B1
(45) Date of Patent: Jun. 11, 2019

(54) TORQUE LIMITING CLOSURE ASSEMBLY

(71) Applicants: Patick Vitello, Pompano Beach, FL (US); Jonathan Vitello, Ft. Lauderdale, FL (US); Timothy Branton Hunt, Miami, FL (US)

(72) Inventors: Patick Vitello, Pompano Beach, FL (US); Jonathan Vitello, Ft. Lauderdale, FL (US); Timothy Branton Hunt, Miami, FL (US)

( * ) Notice: Subject to any disclaimer, the term of this patent is extended or adjusted under 35 U.S.C. 154(b) by 540 days.

(21) Appl. No.: 15/076,254

(22) Filed: Mar. 21, 2016

Related U.S. Application Data (60) Provisional application No. 62/135,210, filed on Mar. 19, 2015.

(51) Int. Cl.
 *A61M 39/20* (2006.01)
 *A61M 39/10* (2006.01)

(52) U.S. Cl.
 CPC ........ *A61M 39/20* (2013.01); *A61M 39/1011* (2013.01); *A61M 39/1055* (2013.01); *A61M 2039/1005* (2013.01)

(58) Field of Classification Search
 CPC ...... A61M 39/1011; A61M 2039/1005; A61M 39/1055; A61M 2005/3104; A61M 2005/3106; A61M 39/20
 See application file for complete search history.

(56) References Cited

U.S. PATENT DOCUMENTS

| | | | |
|---|---|---|---|
| 732,662 A | 6/1903 | Smith | |
| 1,678,991 A | 7/1928 | Marschalek | |
| 1,970,631 A | 8/1934 | Sherman | |
| 2,477,598 A | 8/1949 | Hain | |
| 2,739,590 A | 3/1956 | Yochem | |
| 2,823,674 A | 2/1958 | Yochem | |
| 2,834,346 A | 5/1958 | Adams | |
| 2,875,761 A | 3/1959 | Helmer et al. | |

(Continued)

FOREIGN PATENT DOCUMENTS

| | | |
|---|---|---|
| EP | 0148116 A | 7/1985 |
| WO | WO 2017086607 | 5/2015 |

*Primary Examiner* — Jason E Flick
*Assistant Examiner* — Courtney B Fredrickson
(74) *Attorney, Agent, or Firm* — Malloy & Malloy, P.L.

(57) ABSTRACT

A closure assembly includes torque limit capabilities facilitating the attachment thereof to a medical connector with sufficient tightness to establish a flow stopping or sealing relation with the medical connector. A housing includes a stop member fixed on the interior thereof and rotatable there with into interruptive engagement with a movement restrictor connected to and movable with a closure cap which includes a flow restrictor. Application of a tightening force to the housing will cause rotation of the stop member into interruptive engagement with the movement restrictor and connected flow restrictor causing forced rotation of the flow restrictor onto attachment with the medical connector, while establishing a predetermined tightness. Over-tightening is prevented by disengagement of the stop member from will the movement restrictor or disconnection of the flow restrictor from the corresponding movement restrictor once the predetermined tightness has been established and upon a continuing tightening force being applied to the housing.

14 Claims, 5 Drawing Sheets

(56) References Cited

U.S. PATENT DOCUMENTS

| | | | |
|---|---|---|---|
| 2,888,015 | A | 5/1959 | Hunt |
| 2,952,255 | A | 9/1960 | Hein, Jr. |
| 3,122,280 | A | 2/1964 | Goda |
| 3,245,567 | A | 4/1966 | Knight |
| 3,323,798 | A | 6/1967 | Miller |
| 3,364,890 | A | 1/1968 | Andersen |
| 3,598,120 | A | 8/1971 | Mass |
| 3,610,241 | A | 10/1971 | LeMarie |
| 3,700,215 | A | 10/1972 | Hardman et al. |
| 3,706,307 | A | 12/1972 | Hasson |
| 3,712,749 | A | 1/1973 | Roberts |
| 3,747,751 | A | 4/1973 | Miller et al. |
| 3,872,867 | A | 3/1975 | Killinger |
| 3,905,375 | A | 9/1975 | Toyama |
| 3,937,211 | A | 2/1976 | Merten |
| 4,043,334 | A | 8/1977 | Brown et al. |
| 4,046,145 | A | 9/1977 | Choksi et al. |
| 4,216,585 | A | 8/1980 | Hatter |
| 4,216,872 | A | 8/1980 | Bean |
| 4,244,366 | A | 1/1981 | Raines |
| 4,252,122 | A | 2/1981 | Halvorsen |
| 4,286,591 | A | 9/1981 | Raines |
| 4,313,539 | A | 2/1982 | Raines |
| 4,420,085 | A | 12/1983 | Wilson et al. |
| 4,430,077 | A | 2/1984 | Mittleman et al. |
| 4,457,445 | A | 7/1984 | Hanks et al. |
| 4,521,237 | A | 6/1985 | Logothetis |
| 4,530,697 | A | 7/1985 | Kuhlemann et al. |
| 4,571,242 | A | 2/1986 | Klein et al. |
| 4,589,171 | A | 5/1986 | McGill |
| 4,667,837 | A | 5/1987 | Vitello et al. |
| 4,693,707 | A | 9/1987 | Dye |
| 4,726,483 | A | 2/1988 | Drozd |
| 4,743,229 | A | 5/1988 | Chu |
| 4,743,231 | A | 5/1988 | Kay et al. |
| 4,760,847 | A | 8/1988 | Vaillancourt |
| 4,832,695 | A | 5/1989 | Rosenberg et al. |
| 4,834,706 | A | 5/1989 | Beck et al. |
| 4,842,592 | A | 6/1989 | Caggiani et al. |
| 4,844,906 | A | 7/1989 | Hermelin et al. |
| 4,906,231 | A | 3/1990 | Young |
| 4,919,285 | A | 4/1990 | Roof et al. |
| 5,009,323 | A | 4/1991 | Montgomery et al. |
| 5,049,129 | A | 9/1991 | Zdeb et al. |
| 5,057,093 | A | 10/1991 | Clegg et al. |
| 5,135,496 | A | 8/1992 | Vetter et al. |
| 5,165,560 | A | 11/1992 | Ennis, III et al. |
| 5,230,429 | A | 7/1993 | Etheredge, III |
| 5,267,983 | A | 12/1993 | Oilschlager et al. |
| 5,292,308 | A | 3/1994 | Ryan |
| 5,295,599 | A | 3/1994 | Smith |
| 5,328,466 | A | 7/1994 | Denmark |
| 5,328,474 | A | 7/1994 | Raines |
| 5,356,380 | A | 10/1994 | Hoekwater et al. |
| 5,380,295 | A | 1/1995 | Vacca |
| 5,405,339 | A | 4/1995 | Kohnen et al. |
| 5,458,580 | A | 10/1995 | Hajishoreh |
| 5,468,224 | A | 11/1995 | Souryal |
| 5,531,695 | A | 7/1996 | Swisher |
| 5,540,666 | A | 7/1996 | Barta et al. |
| 5,549,571 | A | 8/1996 | Sak |
| 5,558,648 | A | 9/1996 | Shields |
| 5,584,817 | A * | 12/1996 | van den Haak ...... A61M 5/322 604/110 |
| 5,588,239 | A | 12/1996 | Anderson |
| 5,624,402 | A | 4/1997 | Imbert |
| 5,674,209 | A | 10/1997 | Yarger |
| 5,700,247 | A | 12/1997 | Grimard et al. |
| 5,702,374 | A | 12/1997 | Johnson |
| 5,776,124 | A | 7/1998 | Wald |
| 5,785,691 | A | 7/1998 | Vetter et al. |
| 5,797,885 | A | 8/1998 | Rubin |
| 5,807,343 | A | 9/1998 | Tucker et al. |
| 5,883,806 | A | 3/1999 | Meador et al. |
| 5,884,457 | A | 3/1999 | Ortiz et al. |
| 5,902,269 | A | 5/1999 | Jentzen |
| 5,951,522 | A | 9/1999 | Rosato et al. |
| 5,951,525 | A | 9/1999 | Thorne et al. |
| 5,954,657 | A | 9/1999 | Rados |
| 5,957,166 | A | 9/1999 | Safabash |
| 5,989,227 | A | 11/1999 | Vetter et al. |
| 6,000,548 | A | 12/1999 | Tsals |
| 6,021,824 | A | 2/2000 | Larsen et al. |
| 6,027,482 | A | 2/2000 | Imbert |
| 6,068,614 | A | 5/2000 | Kimber et al. |
| 6,126,640 | A | 10/2000 | Tucker et al. |
| 6,190,364 | B1 | 2/2001 | Imbert |
| 6,193,688 | B1 | 2/2001 | Balestracci et al. |
| 6,196,593 | B1 | 3/2001 | Petrick et al. |
| 6,196,998 | B1 | 3/2001 | Jansen et al. |
| 6,235,376 | B1 | 5/2001 | Miyazaki et al. |
| 6,280,418 | B1 | 8/2001 | Reinhard et al. |
| 6,287,671 | B1 | 9/2001 | Bright et al. |
| 6,322,543 | B1 | 11/2001 | Singh et al. |
| 6,338,200 | B1 | 1/2002 | Baxa et al. |
| 6,375,640 | B1 | 4/2002 | Teraoka |
| 6,394,983 | B1 | 5/2002 | Mayoral et al. |
| 6,485,460 | B2 | 11/2002 | Eakins et al. |
| 6,500,155 | B2 | 12/2002 | Sasso |
| 6,520,935 | B1 | 2/2003 | Jansen et al. |
| 6,540,697 | B2 | 4/2003 | Chen |
| 6,565,529 | B1 | 5/2003 | Kimber et al. |
| 6,581,792 | B1 | 6/2003 | Limanjaya |
| 6,585,691 | B1 | 7/2003 | Vitello |
| 6,592,251 | B2 | 7/2003 | Edwards et al. |
| 6,682,798 | B1 | 1/2004 | Kiraly |
| 6,726,652 | B2 | 4/2004 | Eakins et al. |
| 6,726,672 | B1 | 4/2004 | Hanley et al. |
| 6,755,220 | B2 | 6/2004 | Castellano et al. |
| 6,764,469 | B2 | 7/2004 | Broselow |
| 6,821,268 | B2 | 11/2004 | Balestracci |
| 6,921,383 | B2 | 7/2005 | Vitello |
| 6,942,643 | B2 | 9/2005 | Eakins et al. |
| 7,055,273 | B2 | 6/2006 | Roshkoff |
| 7,141,286 | B1 | 11/2006 | Kessler et al. |
| 7,182,256 | B2 | 2/2007 | Andreasson et al. |
| 7,240,926 | B2 | 7/2007 | Dalle et al. |
| 7,374,555 | B2 | 5/2008 | Heinz et al. |
| 7,404,500 | B2 | 7/2008 | Marteau et al. |
| 7,410,803 | B2 | 8/2008 | Nollert et al. |
| 7,425,208 | B1 | 9/2008 | Vitello |
| 7,437,972 | B2 | 10/2008 | Yeager |
| 7,482,166 | B2 | 1/2009 | Nollert et al. |
| 7,588,563 | B2 | 9/2009 | Guala |
| 7,594,681 | B2 | 9/2009 | DeCarlo |
| 7,632,244 | B2 | 12/2009 | Buehler et al. |
| 7,641,636 | B2 | 1/2010 | Moesli et al. |
| 7,735,664 | B1 | 6/2010 | Peters et al. |
| 7,748,892 | B2 | 7/2010 | McCoy |
| 7,762,988 | B1 | 7/2010 | Vitello |
| 7,766,919 | B2 | 8/2010 | Delmotte |
| 7,802,313 | B2 | 9/2010 | Czajka |
| 7,918,830 | B2 | 4/2011 | Langan et al. |
| 8,079,518 | B2 | 12/2011 | Turner et al. |
| 8,091,727 | B2 | 1/2012 | Domkowski |
| 8,137,324 | B2 | 3/2012 | Bobst |
| 8,140,349 | B2 | 3/2012 | Hanson et al. |
| 8,257,286 | B2 | 9/2012 | Meyer et al. |
| 8,328,082 | B1 | 12/2012 | Bochenko et al. |
| 8,348,895 | B1 | 1/2013 | Vitello |
| 8,353,869 | B2 | 1/2013 | Ranalletta et al. |
| 8,443,999 | B2 | 5/2013 | Reinders |
| D684,057 | S | 6/2013 | Kwon |
| 8,512,277 | B2 | 8/2013 | Del Vecchio |
| 8,556,074 | B2 | 10/2013 | Turner et al. |
| 8,579,116 | B2 | 11/2013 | Pether et al. |
| 8,591,462 | B1 * | 11/2013 | Vitello ................. A61M 5/008 604/111 |
| 8,597,255 | B2 | 12/2013 | Emmott et al. |
| 8,597,271 | B2 | 12/2013 | Langan et al. |
| 8,616,413 | B2 | 12/2013 | Koyama |
| D701,304 | S | 3/2014 | Lair et al. |
| 8,672,902 | B2 * | 3/2014 | Ruan ................. A61M 5/3202 604/192 |

(56) References Cited

U.S. PATENT DOCUMENTS

| | | |
|---|---|---|
| 8,702,674 B2 | 4/2014 | Bochenko |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,945,082 B2 | 2/2015 | Geiger et al. |
| 9,101,534 B2 | 8/2015 | Bochenko |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,272,099 B2 | 3/2016 | Limaye et al. |
| 9,311,592 B1 | 4/2016 | Vitello |
| D756,777 S | 5/2016 | Berge et al. |
| 9,336,669 B2 | 5/2016 | Bowden et al. |
| D759,486 S | 6/2016 | Ingram et al. |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D789,529 S | 6/2017 | Davis et al. |
| 9,687,249 B2 | 6/2017 | Hanlon et al. |
| D797,928 S | 9/2017 | Davis et al. |
| D797,929 S | 9/2017 | Davis et al. |
| 9,855,191 B1 | 1/2018 | Vitello et al. |
| D815,945 S | 4/2018 | Fischer |
| D825,746 S | 8/2018 | Davis et al. |
| 2001/0034506 A1 | 10/2001 | Hirschman et al. |
| 2001/0056258 A1 | 12/2001 | Evans |
| 2002/0023409 A1 | 2/2002 | Py |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0133119 A1 | 9/2002 | Eakins et al. |
| 2003/0146617 A1 | 8/2003 | Franko, Sr. |
| 2003/0183547 A1 | 10/2003 | Heyman |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1* | 4/2008 | Buehler ............... A61M 5/50 604/111 |
| 2008/0106388 A1 | 5/2008 | Knight |
| 2008/0243088 A1 | 10/2008 | Evans |
| 2008/0306443 A1 | 12/2008 | Neer |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0088354 A1 | 4/2013 | Thomas |
| 2013/0237949 A1 | 9/2013 | Miller |
| 2014/0000781 A1 | 1/2014 | Franko, Jr. |
| 2014/0034536 A1 | 2/2014 | Reinhardt et al. |
| 2014/0069829 A1 | 3/2014 | Evans |
| 2014/0135738 A1 | 5/2014 | Panian |
| 2014/0155868 A1 | 6/2014 | Nelson et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0319438 A1 | 11/2017 | Davis et al. |
| 2018/0001540 A1 | 1/2018 | Byun |
| 2018/0089593 A1 | 3/2018 | Patel et al. |

* cited by examiner

TORQUE LIMITING CLOSURE ASSEMBLY

CLAIM OF PRIORITY

This application claims priority to a U.S. provisional patent application having Ser. No. 62/135,210 and filed on Mar. 19, 2015, which is herein incorporated by reference in its entirety.

BACKGROUND OF THE INVENTION

Field of the Invention

This invention is directed to one or more embodiments of a closure assembly which is structured to be connected in flow sealing or stopping relation to a medical connector. The closure assembly includes torque limiting capabilities which facilitate attachment thereof to the medical connector with sufficient tightness to establish the flow stopping connection. Similarly, over-tightening of the closure assembly on the medical connector is completely, or at least substantially, prevented.

Description of the Related Art

In the medical field, it is a relatively common procedure to administer fluids to a patient by syringes, intravenous infusion (IV) infusion devices, medical tubing, etc. As such, administration devices or assemblies are useful in the treatment of a number of medical conditions, in that a variety of fluids and/or medicines can be administered to a patient utilizing such assemblies over a prescribed period of time and in controlled amounts. By way of example, a conventional IV administration assembly typically includes a reservoir or container, in the form of a bottle or more commonly, a flexible material bag, suspended on a pole or like support structure located substantially adjacent to the patient being treated, typically in an elevated relation thereto. In addition, the IV fluid flows from the supported and elevated IV bag to the patient by means of elongated, flexible medical tubing connected at a proximal end to the IV bag and at the other distal end, connected intravenously to the patient by way of a catheter or like structure. The IV delivery tube is also structured to connect at one end to or be interconnected with an appropriate connector, often having somewhat of a "Y" shape, that is associated with the IV assembly and in fluid communication with either the contents of the IV bag or alternatively, with the catheter in use on the patient for intravenous administration of fluids and medicines.

One such connector may be in the form of a female connector attached to the IV bag or other container and disposed in fluid communication with the contents thereof. An appropriate female connector may be, but is not limited to, a female luer connector which at least partially defines, along with a male luer connector, a "luer lock" connector assembly, as is well known in the medical profession. The male connector is secured to the IV delivery tubing, such as at the proximal end, and is specifically structured to be attached to the female connector in a manner which establishes fluid communication with contents of the IV container, and facilitates a flow of the IV fluid from the IV container through the connected male and female connectors. As a result, fluid flow between the patient and the interior of the IV bag is established. As is also well known, various types of valves and/or flow regulating devices may be operatively associated with the IV assembly to regulate the amount of fluid or rate of fluid delivery to the patient during the administration procedure.

In addition, known IV containers or reservoirs may incorporate an additional female luer connector, or other female type connector, disposed in fluid communication with the IV delivery tubing, such as but not limited to at the IV bag. This additional female connector is provided to administer additional liquid agents, such as pain medication, antibiotics, and/or other medicinal compositions, to the IV fluid being delivered to the patient. However, such an additional female connector may remain unused or may be accessed subsequently to the initiation of the IV fluid administration, such as when additional medication or another composition is required or prescribed.

In periods of non-use, it is important to maintain a closure assembly in a closed and fluid sealed condition in order to maintain sterility, and also, the integrity of the contents of the medical device prior to use. With known or conventional closure assemblies, it is sometimes difficult to sufficiently tighten the closure assembly on the medical connector associated with the medical device, even though this is necessary to prevent leakage of the medicine from a discharge port or other portions of the medical connector. On the other hand, it is undesirable to "over-tighten" a closure assembly on a medical connector as such over-tightening may result in some discomfort and/or inconvenience to an individual who has to repeatedly detach a plurality of closure assemblies from corresponding medical connectors over a period of a day or hours/shift worked by the individual.

Therefore, there is a need in the medical field and related art for an efficient, effective and easily applied closure assembly which provides a clear indication that the closure assembly is adequately tightened onto a corresponding medical connector. Similarly, if any such proposed or improved closure assembly were developed, it would preferably also prevent the "over-tightening" of a closure assembly on a medical connector. In addition, the structural and operative features of any such preferred closure assembly, were one developed, should be such as to enable its use with different types of medical connectors of the type commonly used in the medical profession. Finally, it would be ideal if any such proposed closure assembly were also modified so as to include a feature signaling that the assembly has been tampered with, or accessed, so as to help restrict unauthorized access to the medicine or other contents of the medical device with which any such a proposed closure assembly is used.

SUMMARY OF THE INVENTION

The present invention is intended to solve these and other problems that remain in this field of art, and as such, is directed to a closure assembly structured to be operatively attached in flow restricting relation to a "medical connector" or like device. As described in greater detail hereinafter, the structural and operational versatility of the various embodiments of the closure assembly facilitate its flow restricting attachment on needleless syringes, IV assemblies, connectors, medical tubing, other connectors, etc. having different structural configurations.

By way of example only, the "medical connector" to which the closure assembly may be attached may include, but not be limited to, a lure connector, an Enteral connector, Neuraxial connector as well as other connector structures utilized in the medical field and related arts. Moreover, with relatively minor structural modification, the closure assembly of the present invention includes a closure cap which may be connected in flow restricting relation to either a male or female connector including those of the type set forth above and described in greater detail hereinafter.

Figure 1:
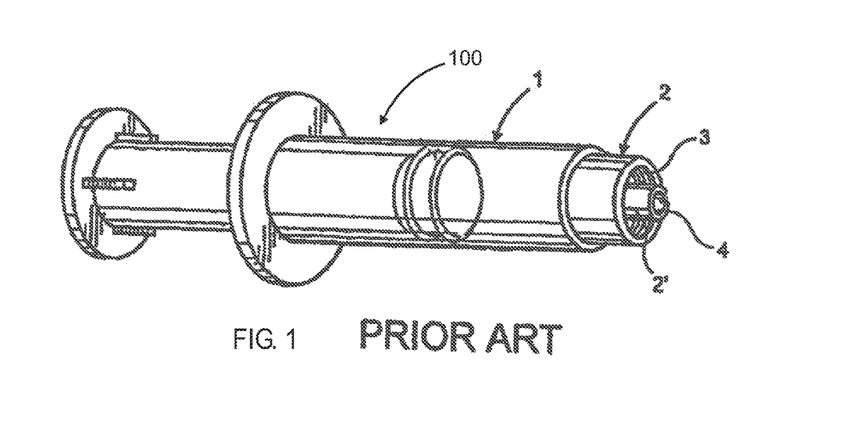
FIG. 1 is a prior art medical device including a medical connector which is representative only of a plurality of additional medical devices and/or medical connectors with which the various embodiments of the closure assembly of the present invention may be utilized.
Figure 2:
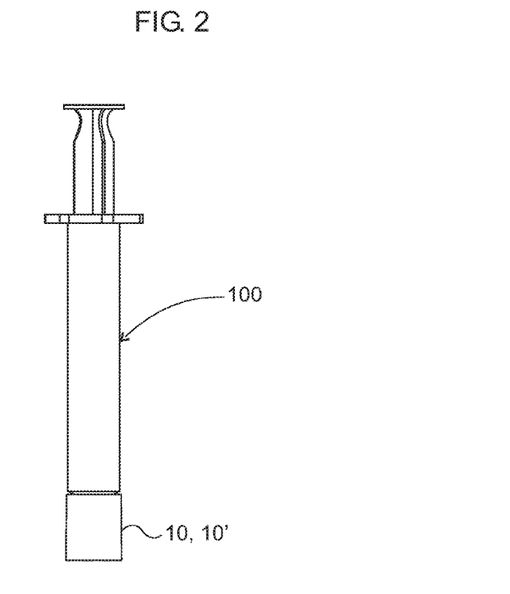
FIG. 2 is a front elevational view of one embodiment of the closure assembly mounted on a medical connector, of the type represented in the prior art device of FIG. 1.

Further by way of example, FIG. 1 is a representation of a conventional, known or prior art medical device in the form of a syringe 100. As such, the syringe 100 includes a fluid containing barrel 1 and a medical connector, generally indicated as 2 at a discharge end thereof. Moreover, the medical connector 2 may assume a "male" configuration including an elongated nozzle 2' terminating in an open discharge port 4, through which the contents of the barrel 1 is discharged when the syringe 100 is in use. Additional features which may or may not be included in a conventional medical device or syringe 100 are interior threaded surfaces or like connecting with portions 3. It is again emphasized that the prior art medical device or syringe of FIG. 1 is representative only of a variety of different medical devices, medical connectors, etc. with which the various embodiments of the closure assembly of the present invention may be used.

As commonly recognized in the medical field, a closure assembly, to be effective, should be mounted or attached on a corresponding medical connector in a manner which prevents leakage from the medical connector. Therefore, the closure assembly must be attached with sufficient "tightness" that a flow restricting portion thereof is connected in flow stopping relation to the medical connector. However, if excessive torque force is applied to the closure assembly during attachment, it may be connected to a corresponding medical connector in a manner which is "overly-tight". Such an "over-tight" attachment presents additional problems relating to the difficulty and possible discomfort which may result when attempting to remove the closure assembly from the medical connector.

Accordingly, the one or more preferred embodiments of the closure assembly of the present invention is structured to effectively limit or at least partially control the amount of torque force applied to the closure assembly as it is being attached to the medical connector. Such effective limiting or control of torque force will result in the closure assembly being attached to the medical connector with sufficient tightness to prevent leakage and stop fluid flow from the medical connector. In addition, the structural and operational versatility of the various embodiments of the closure assembly of the present invention is also structured to prevent an excessive torque force being applied to the closure assembly thereby restricting the possibility of "over-tightening" of the closure assembly on the medical connector.

Therefore, at least one embodiment of the closure assembly of the present invention includes an outer cover or housing having an at least partially hollow interior. In addition, a stop member is fixedly disposed on the interior of the housing so as to rotate with the housing. Also, one or more preferred embodiments of the closure assembly comprises a closure cap which includes a flow restrictor, where in the closure cap and included flow restrictor are rotationally disposed, as a single unit, within the interior of the housing. As explained in greater detail hereinafter, representative embodiments of the flow restrictor may be in the form of a female flow restrictor structured to receive a male medical connector such as, but not limited to, the type medical connector set forth in the prior art representation of FIG. 1. However, with minor structural modification and without affecting the intent and scope of the present invention, the flow restrictor may be in the form of a male plug dimensioned and configured to be attached in flow stopping relation to a female medical connector.

It is also emphasized that is used herein, the term "flow restricting" is meant to include the flow restrictor portion of the closure assembly being attached to a corresponding medical connector with sufficient "tightness" to stop the flow of fluid or leakage from the corresponding medical connector.

One or more embodiments of the closure assembly also include a movement restrictor attached to the closure cap and flow restrictor and rotatable therewith on the interior of the housing. Accordingly, as the closure assembly is being attached, such as by being rotated onto the medical connector, a discharge port of the medical connector will be disposed in flow restricting engagement with the flow restrictor. Attempts to adequately tighten the closure assembly on the medical connector will commonly include a torque force being exerted on the closure assembly and accordingly on the flow restrictor. Such a torque force will cause rotation of the housing and stop member, such that the stop member will interruptively engage the movement restrictor connected to the flow restrictor. As a result, the closure cap will be forced to rotate onto the medical connector until a sufficient tightness therebetween has been established.

Therefore, as the closure assembly is rotated onto the medical connector, the flow restrictor will be forced to rotate within the interior of the housing due to the engagement between the movement restrictor and the stop member. However, after tightening and upon an individual continuing to exert a tightening force on the closure assembly, the stop member will bypass and become detached from the movement restrictor due to the resistance provided by the now adequately tight connection between the flow restrictor and the medical connector. Accordingly, the movement restrictor may include a flexible construction sufficient to allow a bending or flexure of the movement restrictor, as set forth in greater detail hereinafter. Therefore, upon a continued application of a torque force or sufficient tightening force on the housing and stop member of the closure assembly, the stop member will engage first the movement restrictor causing a forced rotation of the flow restrictor and or closure cap until a sufficient tightening has occurred. Thereafter, due to the flexure of the movement restrictor, the stop member will be forced to bypass or disengage the movement restrictor wants the flow restrictor is tightly secured on the medical connector. Such disengagement of the stop member from the movement restrictor will be an indication to a user that a sufficient tightening force has been exerted on the closure assembly to dispose the flow restrictor in "flow stopping" attachment to the corresponding medical connector.

As also explained in greater detail hereinafter, the movement restrictor may be structured to generate an appropriate sound, thereby providing and "audible indication" as it passes over and/or becomes detached from the stop member. Such "audible indication" may be in the form of a "snap-like" sound or other appropriate sound which is loud enough to be discernible by an individual attaching the closure assembly to the corresponding medical connector. Therefore, upon a user detecting such sound or "audible indication" the user will be made aware that sufficient "tightening force" has been exerted on the closure assembly to accomplish a fluid flow stopping attachment between the flow restrictor and a fluid flow port of the medical connector.

Yet another preferred embodiment of the closure assembly is structured to demonstrate a sufficient tightness of the closure assembly and flow restrictor on a corresponding medical connector in a different manner. More specifically, in this additional preferred embodiment, the flow restrictor is removably connected, such as by a frangible connection, to a remainder of the closure cap. Further, the movement restrictor in this embodiment is fixedly attached to the remaining portion of the closure cap. In addition, the movement restrictor is also disposed to engage the stop member as the stop member rotates along with the housing as the closure assemblies being attached to the medical connector. Interruptive engagement of the stop member with the movement restrictor of this additional embodiment will cause a forced rotation of the closure cap and connected flow restrictor until a sufficient tightening has occurred between the flow restrictor and the medical connector. Thereafter, a continuation of a tightening force being applied to the housing and a resulting continued rotation of the stop member will cause an excessive force to exerted on the fixed movement connector. This excessive force will eventually be transferred or exerted on the flow restrictor.

Accordingly, when a sufficient tightening force is exerted on the closure assembly, engagement between the movement restrictor and the stop member may at least temporarily and/or partially restrict or stop rotation of the housing and stop member closure assembly relative to the medical connector. This will also be an indication to a user that a sufficient tightening force has been applied to the closure assembly to connect the flow restrictor to the corresponding medical connector in a manner which prevents leakage and stops fluid flow from the discharge port/medical connector.

Further, due to the fact that the movement restrictor is fixed to the closure cap and the flow restrictor is removably and/or frangibly connected to a remainder of the closure cap, the continued exertion of a torque force or tightening force on the closure assembly will result in a continued rotation of the stop member. If such the housing and stop member continue to rotate once adequate tightening has been accomplished between the flow restrictor and the medical connector, the flow restrictor will become detached from the remainder of the closure cap, as well as the housing. Accordingly, an over tightening of the closure assembly will be prevented by such detachment of the flow restrictor from the housing. When so detached, the flow restrictor will remain on the fluid flow port of the medical connector and possibly pass outwardly from the interior of the housing. However, due to the comparatively small size of the flow restrictor it will be difficult to rotate, unthread or otherwise detached the flow restrictor from the fluid flow port of the connector.

Additional structural and operational features of the one or more embodiments of the closure assembly of the present invention include the stop member preferably being in the form of a "cliff and ramp" structure. As such, the aforementioned movement restrictor associated with the various embodiments of the closure assembly is cooperatively disposed, configured, dimensioned and structured with the cliff and ramp stop member to allow rotation of the movement restrictor, and flow restrictor to which it is attached, in only a single direction without the rotation thereof being restricted. However, rotation in an opposite direction, such as when attempting to tighten the closure assembly on a corresponding medical connector, will result in interruptive engagement of the stop member with the movement restrictor connected to the flow restrictor. Such interruptive engagement of the stop member will force rotation of the movement restrictor and connected flow restrictor until an adequate tightening has occurred between the flow restrictor in the medical connector. Once such adequate tightening is accomplished, continued rotation of the housing will force the Cliff and ramp stop member to bypass or disengage from the flow restrictor in at least one preferred embodiment of the closure assembly, as set forth above.

Yet additional preferred features associated with one or more preferred embodiments of the closure assembly include a tamper evident feature. More specifically, a retaining structure, preferably in the form of an indicator ring is removably and/or frangibly attached to the interior surfaces of the housing. Such indicator ring is disposed between and access opening of the housing and the flow restrictor. In such a location, the indicator ring or like retaining structure serves to maintain the closure cap and included flow restrictor within the interior of the housing, prior to its attachment to a medical connector. However, upon an authorized or unauthorized removal of the housing from the closure cap, the indicator ring of the retaining structure will also be detached from the housing and be disposed in a mounting and/or surrounding, relation on at least a portion of the medical connector. As such, a clear visual indication of use and/or tampering will be apparent.

Therefore, the various preferred embodiments of the closure assembly of the present invention are structured to facilitate their attachment to a corresponding medical connector with sufficient "tightness" to stop fluid flow and/or prevent leakage from the medical connector. As a result, the closure assemblies of the present invention are structured to include "torque limiting" or "torque indicating" capabilities, as the closure assembly is being attached to the corresponding medical connector.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented in the accompanying FIGS. 2-11, the present invention is directed to a closure assembly generally indicated as 10 in the embodiment of FIGS. 3-8 and generally represented as 10' in the embodiment of FIGS. 9-11A. As such, the various preferred embodiments of the closure assembly of the present invention are structured for flow stopping connection to a medical device 100, and more specifically, such as to a medical connector or syringe 2 associated therewith as shown in FIG. 1. It is emphasized that the prior art medical device 100, as represented in FIG. 1, is provided for purposes of clarity and by way of example only. It is further emphasized that the "medical connector" to which the closure assembly 10 may be attached may include, but not be limited to, a lure connector, Enteral connector, Neuraxial connector, as well as other connector type structures including a needleless syringe, IV assembly, medical tubing, etc., commonly utilized in the medical and related arts.

Therefore and with primary reference now to the embodiment of the invention illustrated in FIGS. 3-8, the closure assembly 10 includes an outer cover or housing 12 having an open access end 14 and an oppositely disposed closed end 16. Further, the housing 12 includes an at least partially hollow interior that is dimensioned and configured to movably and/or rotationally receive and retain a closure cap, generally indicated as 18 therein. The closure cap 18 includes a flow restricting portion or "flow restrictor" 20, as perhaps best shown in FIGS. 3 and 4, which is represented as including a female configuration. As such, the female flow restrictor 20 is structurally adapted to receive an elongated male-type nozzle 2' such as, but not limited to, that represented in FIG. 1 as the prior art medical device 100 and medical connector 2. Further, the closure cap 18 includes additional or remaining portions, such as a skirt 22, and a movement restrictor generally indicated as 24, including one or more spring tabs 34, to be described in greater detail hereinafter.

Figure 4:
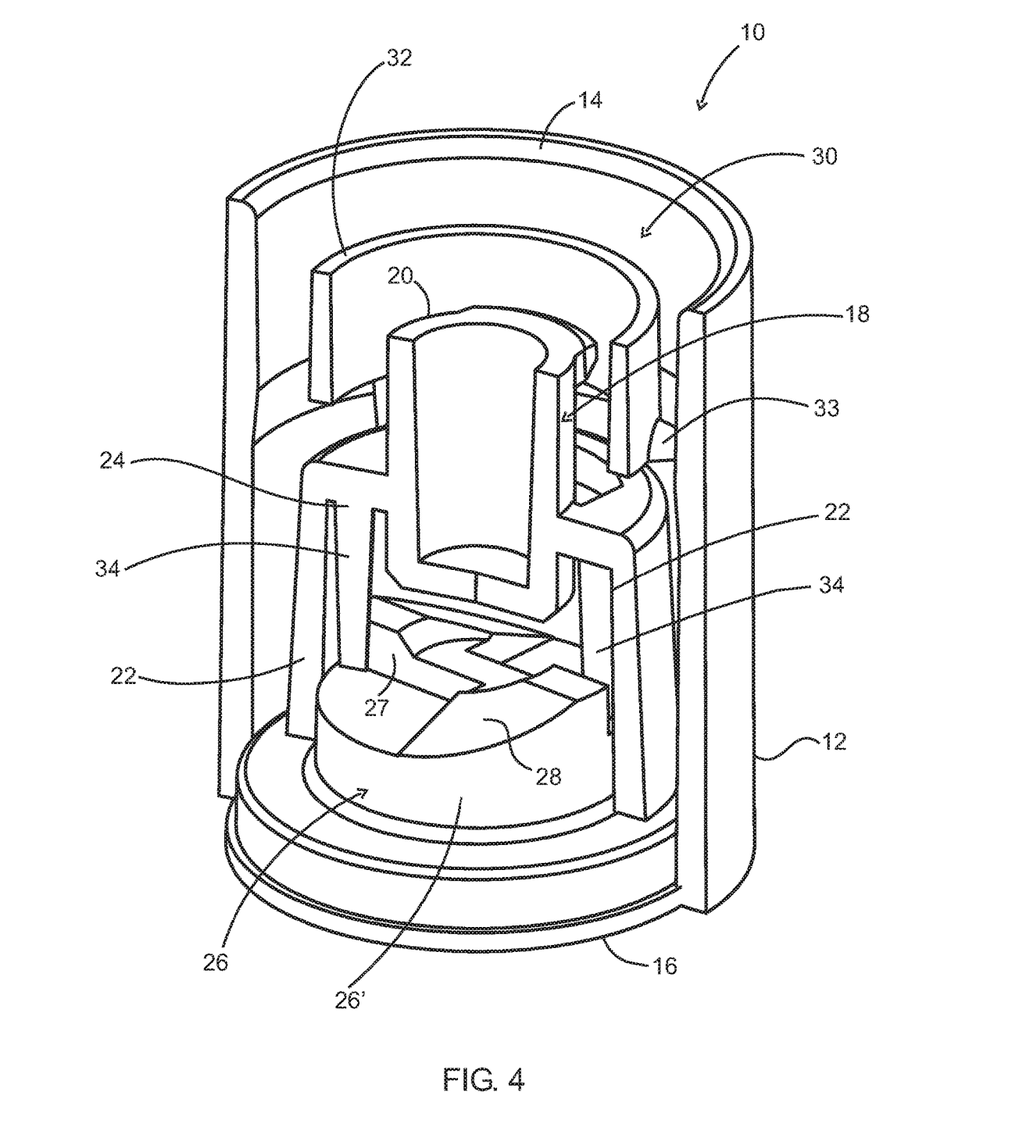
FIG. 4 is an interior perspective view of the embodiment of FIG. 2.
Figure 5:
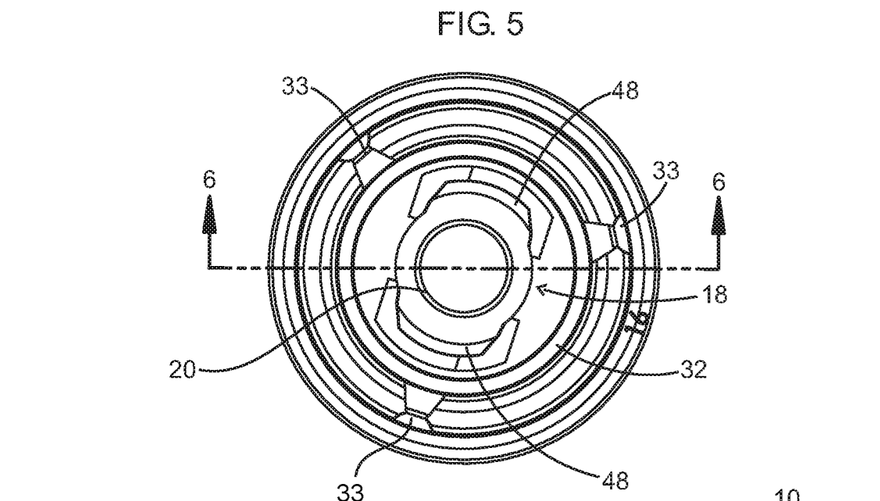
FIG. 5 is a top interior view of one embodiment of the closure assembly.
Figure 6:
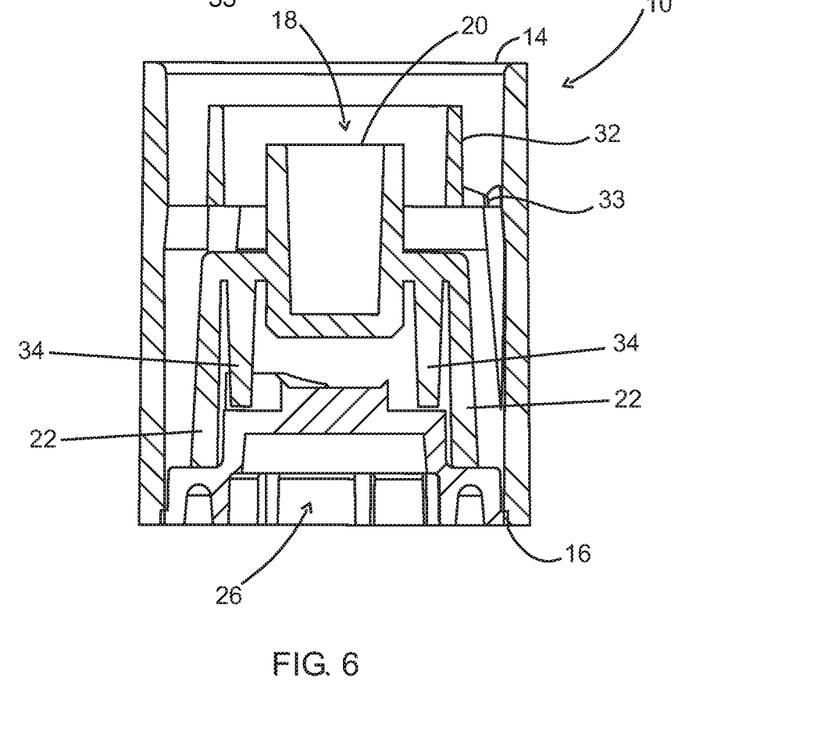
FIG. 6 is a side interior view of the embodiment of FIG. 5 as taken along the lines 6-6 shown therein.
Figure 7:
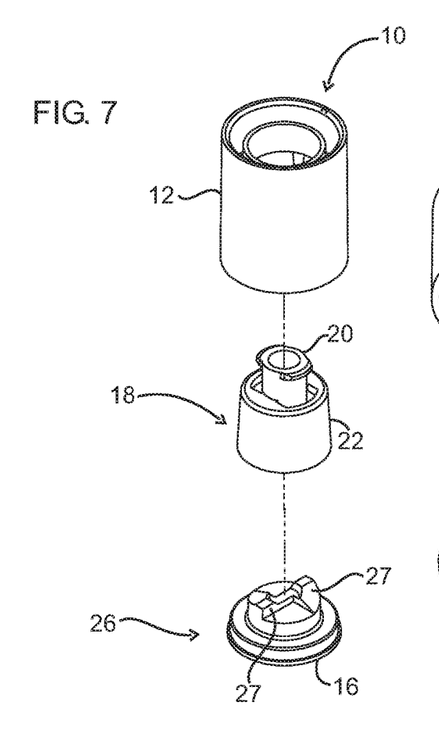
FIG. 7 is a top perspective view in exploded form of the operative components of the embodiment of FIGS. 3 and 6.
Figure 8:
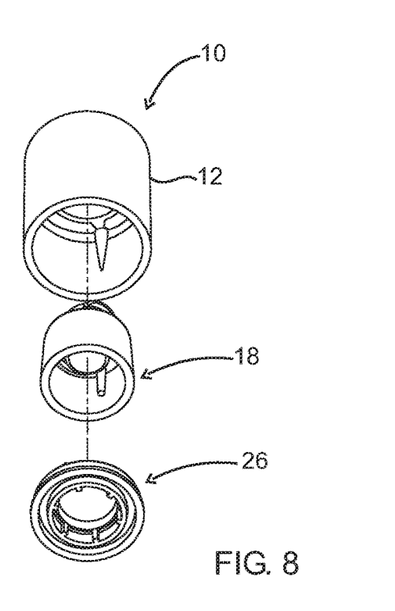
FIG. 8 is a bottom perspective view in exploded form of the embodiment of FIGS. 6 and 7.
Figure 9:
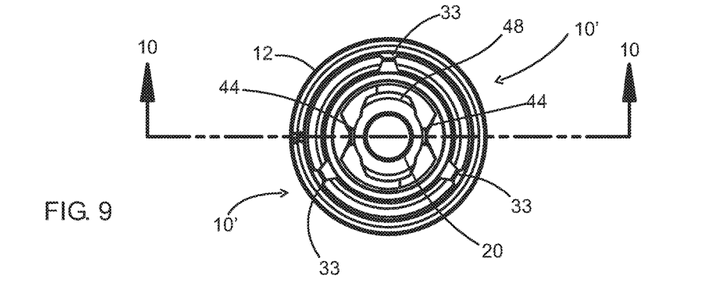
FIG. 9 is a top interior view of another preferred embodiment of the closure assembly of the present invention.
Figure 10:
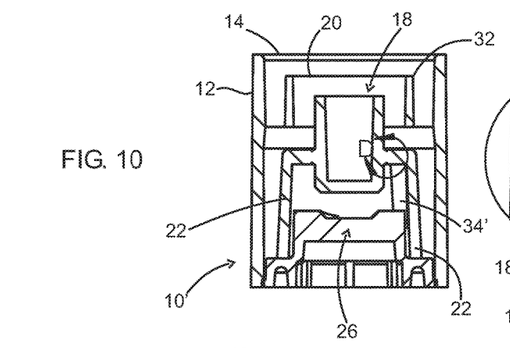
FIG. 10 is a sectional view of the embodiment shown in FIG. 9, as taken along the lines 10-10 of FIG. 9.
Figure 10A:
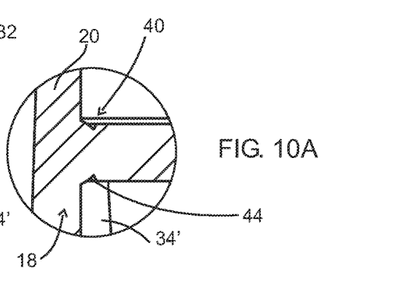
FIG. 10A is a detailed view of a frangible connection of the embodiment of FIG. 10.
Figure 11:
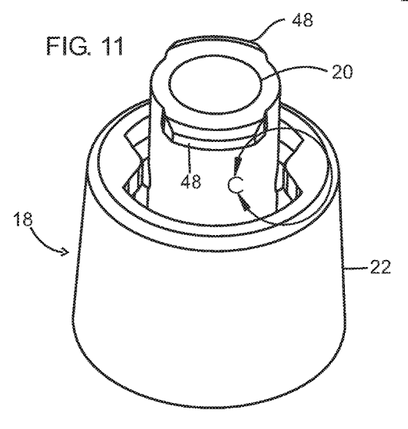
FIG. 11 is a top perspective view of the closure cap, associated with the embodiments of FIGS. 10-10A.
Figure 11A:
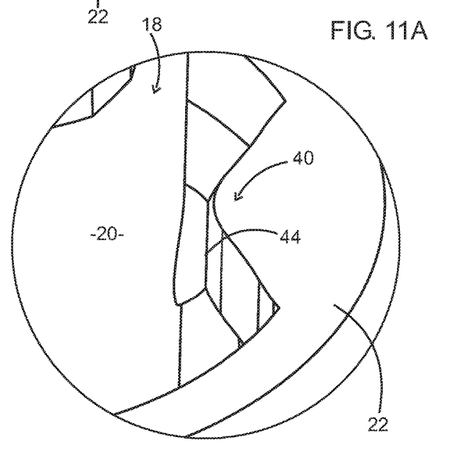
FIG. 11A is a detail view in perspective of a frangible connection associated with the embodiment of FIGS. 10 and 10A.

As shown in FIG. 4, the housing 12 includes a stop member generally indicated as 26, that is fixedly attached or connected on the interior thereof and rotatable with the housing 12, such as when the closure assembly 10 is being attached to a medical connector. In addition, the stop member 26 is preferably in the form of a "cliff and ramp" structure including one or more cliff segments 27 and one or more ramp segments 28. As will be explained in greater detail hereinafter, the cliff and ramp stop member 26 will allow free rotation of the closure cap 18 in one direction, such as a counterclockwise direction, but will at least minimally restrict rotation of the closure cap 18 and flow restrictor 20 in the opposite or clockwise direction, due to an interaction of the cliff and ramp segments 27 and 28, respectively, with the movement restrictor 24 and spring tabs 34. In more specific terms, upon a rotation of the housing 12, the fixedly attached stop member will rotate therewith. Such rotation of the stop member 26 will result in an interruptive engagement of the stop member 26 with the movement restrictor 24 connected to the closure cap 18 and flow restrictor 20.

Figure 3:
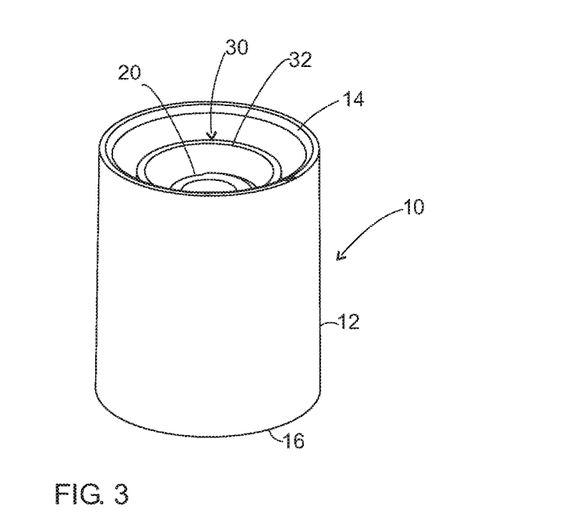
FIG. 3 is a perspective view of one embodiment of the closure assembly of the present invention.

The closure assembly 10 may also be structured to have "tamper evident" features, generally indicated as 30, perhaps best shown in FIGS. 3 and 4, including an indicator ring 32 disposed at least partially between the access opening 14 of the housing 12 and the closure cap 18. In such a position, the indicator ring 32 may be described as being disposed in retaining relation to the closure cap 18 which is movably, and more specifically, rotationally disposed within the interior of the housing 12.

As indicated above, and represented throughout the Figures, the cliff and ramp stop member 26 is disposed on the interior of the housing 12 in interruptive relation and/or interruptive engagement with the aforementioned movement restrictor 24 and spring tabs 34 connected to and rotational with the closure cap 18 and the flow restrictor 20. As also clearly represented, the movement restrictor 24 includes the at least one but possibly plurality of spring tabs 34, each of which includes a flexible construction. Upon rotation of the housing 12 and stop member 26 in a predetermined direction, the stop member will come into interruptive engagement with the spring tabs 34. As should be apparent, rotation of the stop member 26 in one direction will result in an interruptive engagement with one or more of the spring tabs 34 with the cliff segment 27.

However, and still referring to FIG. 4, rotation in the opposite direction will result in engagement between the ramp segments 28 with corresponding ones of the spring tabs 34. When attempting to connect and tighten the closure assembly 10 on the corresponding medical connector, the housing will be rotated, preferably in a clockwise direction thereby causing interruptive engagement with the cliff segment 27 and the one or more correspondingly disposed spring tabs 34. As a result, the closure cap 18 and connected flow restrictor 20 will be forced to rotate with the housing 12 onto the corresponding medical connector. When a sufficient tightening force has been applied to acquire a flow stopping connection between the flow restrictor 20 and the medical connector, a movement restricting force will be applied to the closure cap 18 and flow restrictor 20. A continued exertion of the tightening force and/or rotation of the housing 12 will result in the stop member, and more specifically, the cliff segment thereof by passing the correspondingly positioned one or more spring tabs 34. This will provide an indication that an adequate tightening force has been accomplished and a flow stopping connection has been achieved between the flow restrictor 20 and the medical connector.

Due to each of the one or more tabs 34 having sufficient flexibility, the one or more spring tabs 34 will bend or flex a sufficient degree to allow the stop member 26 to pass there beneath or there beyond and otherwise disengage from the corresponding one or more spring tabs 34. Accordingly, the flexible construction of the one or more tabs 34 may be accurately described as providing "spring-like" capabilities and thereby be described as a spring member or spring tab.

In use, a medical connector 100 such as shown in FIG. 1 and more specifically, the nozzle 2' thereof is inserted within the flow restrictor 20. The closure assembly 10, and more specifically, the housing 12 may then be rotated to securely "tighten" the closure cap 18 in flow restricting relation to the discharge port, such as at 4 of the medical connector 2. However in order to prevent leakage from the discharge port 4, the closure assembly 10 must be sufficiently "tightened" to establish a flow stopping sealing engagement between the flow restrictor 20 and the discharge port 4. In doing so, the housing 12 and the attached stop member 26 may be rotated, such as in a clockwise direction, with a sufficient torque or tightening force to establish such a flow stopping sealing engagement.

The provision of the cliff and ramp stop member 26 will force the closure cap 18 to rotate along with the stop member, due to the interruptive engagement between the stop member 26 and a corresponding spring tabs 34. This occurs because one or both of the movement restrictor or spring tabs 34 will engage a correspondingly positioned cliff segment 27 of the ramp and cliff stop member 26. When a sufficient tightening force is exerted on the flow restrictor 20, due to the concurrent clockwise rotation of the housing 12 and flow restrictor 20, the aforementioned flow stopping, sealing engagement between the flow restrictor 20 and the medical connector 2 will be established.

However, the closure assembly 10 of the present invention is also structured to prevent or substantially prevent an "over-tightening". More specifically, the flexible construction or spring like capability of the movement restrictor spring tabs 34 will allow their flexure or bending, upon a continuation of the tightening force being exerted on the flow restrictor 20. Such flexure or bending will allow the stop member 26 to bypass and become detached from the corresponding one or more spring tabs 34. Continued rotation of the housing 12 and stop member 26 will allow the one or more spring tabs 34 to slide over the top of the corresponding ramp segments 27 and down the contiguously disposed ramp segments 28. In turn, this will allow a continued rotation of the stop member 26 and housing 12, while the fluid restrictor 20 is attached with appropriate thickness on the medical connector. Therefore, the bending or flexure of the movement restrictor tabs 34 will result in a disengagement of the flow restrictor 20 and the attached movement restrictor 24 from the stop member 26. Accordingly, a continued exertion of the tightening force and/or a continued excessive torque force exerted on the housing 12 will prevent an over-tightening of the flow restrictor 20 and/or closure assembly 10 onto a corresponding medical connector, such as at 2.

Yet additional features associated with both the embodiments of the closure assembly as at 10 and 10' include the provision of the skirt 22 which represents an at least partially defines a remaining portion of the closure cap 18. As represented throughout the figures, the skirt 22 is disposed in at least partially surrounding relation to an exterior wall or surface portion 26' of the cliff and ramp stop member 26. Due to the fact that the closure cap 18 is movable or more specifically rotational within the interior of the housing 12 it may become misaligned or inadvertently displaced from its intended, operative position relative to the access opening 14 as well as the stop member 26. Therefore, the at least partial surrounding orientation of the correspondingly disposed open end of the skirt 22 serves to maintain and operative alignment of the flow restrictor 20 relative to the stop member 26, the access opening 14, the housing 12 and other operative components associated there with.

Yet another preferred embodiment of the closure assembly is generally represented as 10' in FIGS. 9-11A. As should be apparent, the closure assembly 10' includes many of the similar or substantially equivalent structural components as the closure assembly 10 described above with reference to FIGS. 3-8. More specifically, the closure assembly 10' includes an outer housing 12 having a stop member 26, preferably in the form of a cliff and ramp structure, fixedly disposed on the interior of the housing 12 and rotationally movable therewith. In addition, a closure cap generally indicated as 18, including a flow restrictor 20, is disposed on the interior of the housing 12 and is rotational bowl relative to or with the stop member 26. Further, the closure cap includes a movement restrictor including at least one fixed tab 34', which is connected to a remaining portion of the closure cap 18 such as the skirt 22. The cliff and ramp stop member 26 and the at least one movement restrictor tab 34' are cooperatively dimensioned, configured and structured so as to allow or facilitate rotation of the closure cap 18 relative to the stop member 26 in one direction, wherein the movement restrictor tab 34' will engage one or more of the ramp segments 28 and slide there over. However, rotation of the closure cap 18 and the connected movement restrictor tab 34' in the opposite direction will result in the restrictor tab 34' engaging one or more of the cliff segments 27. Such interruptive engagement between a restrictor tab 34' and a cliff segment 27 will result in a forced rotation of the closure cap 18 and flow restrictor 20 with the stop member 26 and housing 12.

One structural feature of the closure assembly 10' as being distinguished from the closure assembly 10 is the structuring of the at least one restrictor tab 34' to have a substantially rigid, substantially non-flexible or substantially non-resilient construction. As a result, the exertion of a tightening force on the housing 12 will eventually result in a forced rotation of the closure cap 18, due to interruptive engagement between the stop member 26 and the movement restrictor tab 34'. This forced rotation of the closure cap 18 and flow restrictor 20 will result in a tightening of the flow restrictor 20 on the corresponding medical connector.

Additional distinguishing structural features of the closure assembly 10' include the at least one movement restrictor tab 34' being fixedly connected to a remaining portion of the closure cap 18, such as the skirt 22. As set forth above, the closure tab 34' has a substantially rigid construction and/or structural integrity with comparatively little or minimal flexibility. Further, the stop member 26 including the cliff and ramp structure is disposed in interruptive relation to the rotational path of the at least one restrictor tab 34'. Accordingly, rotation of the stop member 26 with the housing 12 will result in the forced rotation of the closure cap 18, flow restrictor 20 and movement restrictor tab 34' due to interruptive engagement between the movement restrictor 34' and the stop member 26. Accordingly, rotation of the housing 12, such as in a clockwise direction, will result in the movement stop member 26 into the noted interruptive engagement with the restrictor tab 34'. This in turn will force continued rotation of the closure cap 18 due to the fact that the movement restrictor tab 34' is attached to the closure cap 18, as set forth above.

However, unlike the closure assembly 10, the flow restrictor 20 of the closure assembly 10' is removably connected, as at 42, to a remainder of the closure cap 18, such as to the skirt 22. More specifically, the removable connection 42 may be more specifically defined as at least one but more practically a plurality of frangible connections 44 disposed and structured to removably interconnect the flow restrictor 20 to a remaining portion of the closure cap 18, such as at the skirt 22. Therefore, upon an attempted mounting of the closure assembly 10' to the corresponding medical connector, as at 2, a tightening force will be exerted on the flow restrictor 20. Such tightening force will cause a forced rotation of the flow restrictor 20 and a remainder of the closure cap 18 until a sufficient tightening connection between the flow restrictor 20 and the medical connector has been established. As set forth repeatedly herein such a sufficient or predetermined tightening connection is meant to include a flow stopping connection between the flow restrictor 20 and the medical connector and/or discharge port associated there with.

However, due to the fact that the flow restrictor 20 is removably and/or frangibly connected, as at 40, to a remaining portion or skirt 22 of the closure cap 18, the continued exertion of such a tightening force and resulting continued rotation of the housing 12 and stop member 26, once an adequate or predetermined tightening has been accomplished, will result in a breakage of the one or more frangible connections 44 and a detachment of the flow restrictor 20 from the remainder of the closure cap 18. Accordingly, an over-tightening of the closure assembly 10' on a corresponding medical connector will be prevented. It is to be understood that the structuring of the one or more frangible connections 44 is variable to accommodate different predetermined tightening forces required to be applied to the housing 12 necessary to accomplish a sealing or fluid flow stopping engagement between the flow restrictor 20 and the corresponding medical connector.

As with the embodiment of the closure assembly 10, the closure assembly 10' also includes the positioning of the skirt 22 relative to the stop member 26 to accomplish and operative alignment of the flow restrictor 20, set forth above. In addition, the closure assembly 10' also includes a retaining structure which may be in the form of the indicator ring 32 being removably attached by at least one, but preferably a plurality of frangible connectors 33.

Yet additional structural and operative features may be associated with a selected one or each of the closure assemblies 10 and 10'. More specifically, an exterior surface of the flow restrictor 20 may include outwardly projecting lips, partial thread segments or other appropriate projections, as at 48. These projections 48 are disposed and dimensioned to the rotationally engage and be connected, as by a threaded connection, to interior threaded portions or surfaces 3 which may be found on a medical connector 2 of different types of conventional medical devices 100, as represented in FIG. 1.

Therefore, the plurality of preferred embodiments of the closure assembly 10, 10', etc. of the present invention includes numerous structural and operative features which are believed to enhance the effectiveness of closure assemblies which are structured to be attached to different types of medical connectors in a flow stopping manner.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure assembly structured for attachment to a medical connector, said closure assembly comprising:
   a housing including a stop member fixedly attached to said housing on an interior, adjacent a closed end thereof and rotational therewith,
   a cap including a flow restrictor structured for flow stopping connection with the medical connector, said cap rotationally disposed within said housing,
   a movement restrictor comprising at least one resilient spring tab connected to said cap and rotational therewith within said housing,
   said stop member comprising a cliff and ramp structure disposed in interruptive, rotating engagement with said movement restrictor upon rotation of said cliff and ramp structure with said housing,
   said movement restrictor and said cliff and ramp structure cooperatively structured for free rotation relative to one another in a single direction and restrictive rotation relative to one another in a direction opposite to said single direction,
   said interruptive, rotating engagement comprising a forced rotation of said cap and said flow restrictor with said housing, concurrent to a predetermined tightening force exerted on said housing, and
   said at least one resilient spring tab and said cliff and ramp structure cooperatively structured for disengagement therebetween and a resumed rotation of said cliff and ramp structure in said opposite direction, concurrent to a continuation of said predetermined tightening force exerted on said housing.

2. The closure assembly as recited in claim 1 wherein said at least one resilient spring tab comprises an at least partially flexible construction including a sufficient flexibility to disengage said cliff and ramp structure upon said continuation of said predetermined tightening force being exerted on said housing.

3. The closure assembly as recited in claim 2 wherein said at least one resilient spring tab is structured to generate an audible indicator upon disengagement of said at least one resilient spring tab from said cliff and ramp structure.

4. The closure assembly as recited in claim 1 wherein said disengagement of said movement restrictor comprises an at least partially sliding passage of said cliff and ramp structure with and beyond said at least one spring tab.

5. The closure assembly as recited in claim 1 wherein said cap further comprises a skirt, including an open end disposed in at least partially surrounding relation to said stop member, said skirt being rotational with said flow restrictor, with and relative to said stop member.

6. The closure assembly as recited in claim 5 wherein said skirt and said stop member are cooperatively disposed and structured to at least partially define an operative alignment of at least said flow restrictor and said stop member.

7. The closure assembly as recited in claim 5 wherein said skirt is disposed in rotational relation to an exterior surface of said cliff and ramp structure; said skirt and said cliff and ramp structure cooperatively disposed and structured to at least partially define an operative alignment between at least said movement restrictor and said stop member.

8. The closure assembly as recited in claim 1 further comprising a retainer structure removably disposed within said housing in retaining relation with at least said flow restrictor.

9. The closure assembly as recited in claim 8 wherein said retainer structure is removably connected to an interior surface of said housing; said retainer structure disposed and structured to retain said cap within said housing in rotational relation to said stop member.

10. The closure assembly as recited in claim 1 wherein said continuation of said predetermined tightening force comprises a force sufficient to over-tighten said flow restrictor on the medical connector.

11. The closure assembly as recited in claim 1 further comprising a retainer structure removably disposed within said housing in removable retaining relation with at least said flow restrictor.

12. The closure assembly as recited in claim 11 wherein said retainer structure comprises an indicator ring removably connected to an interior surface of said housing; said indicator ring disposed and structured to removably retain said cap within said housing in interruptive relation to said stop member.

13. A closure assembly structured to limit torque force applied thereto when attached to a medical connector, said closure assembly comprising:
- a housing including a stop member; said stop member comprising a cliff and ramp structure fixedly and interiorly attached adjacent a closed end of said housing and rotational therewith,
- a cap including a flow restrictor disposed within said housing and structured for flow stopping connection with the medical connector, said cap and said flow restrictor rotational with and relative to said cliff and ramp structure and said housing,
- a movement restrictor connected to said cap and movable therewith within said housing,
- said movement restrictor and said cliff and ramp structure cooperatively structured for free rotation relative to one another in a single direction and restrictive rotation relative to one another in a direction opposite to said single direction,
- said cliff and ramp structure disposed in interruptive, rotating engagement with said movement restrictor upon concurrent rotation of said stop member and said housing,
- said interruptive, rotating engagement comprising a forced rotation of said cap and said flow restrictor with said housing concurrent to a predetermined tightening force exerted on said housing,
- said predetermined tightening force being sufficient to secure said flow restrictor in flow stopping engagement on the medical connector, and
- said movement restrictor and said cliff and ramp structure cooperatively structured for disengagement therebetween and a resumed rotation of said cliff and ramp structure in said opposite direction, concurrent to a continuation of said predetermined tightening force exerted on said housing.

14. The closure assembly as recited in claim 13 wherein said movement restrictor comprises at least one resilient spring tab connected to said cap and rotatable with said flow restrictor within said housing.

* * * * *